(12) United States Patent
Moon et al.

(10) Patent No.: US 8,440,433 B2
(45) Date of Patent: May 14, 2013

(54) CORYNEBACTERIUM GLUTAMICUM ENHANCED EXPRESSION OF MOAA GENE ENCODING MOLYBDENUM COFACTOR BIOSYNTHESIS ENZYME A AND METHOD FOR PRODUCING L-LYSINE USING THE SAME

(75) Inventors: Jun-Ok Moon, Seoul (KR); Jae-Woo Jang, Suwon-Si (KR); So-Yeon Rah, Seoul (KR); Sang-Jo Lim, Incheon (KR); Jong-Soo Choi, Seoul (KR); Young-Hoon Park, Seongnam-Si (KR); Hyung-Joon Kim, Seoul (KR)

(73) Assignee: CJ Cheiljedang Corp., Seoul (KR)

( * ) Notice: Subject to any disclaimer, the term of this patent is extended or adjusted under 35 U.S.C. 154(b) by 516 days.

(21) Appl. No.: 12/520,684

(22) PCT Filed: Dec. 20, 2007

(86) PCT No.: PCT/KR2007/006701
§ 371 (c)(1),
(2), (4) Date: Jun. 16, 2010

(87) PCT Pub. No.: WO2008/075914
PCT Pub. Date: Jun. 26, 2008

(65) Prior Publication Data
US 2010/0273222 A1    Oct. 28, 2010

(30) Foreign Application Priority Data

Dec. 21, 2006   (KR) .................. 10-2006-0132087

(51) Int. Cl.
*C12P 13/08* (2006.01)
*C12N 9/00* (2006.01)
*C12N 1/20* (2006.01)
*C12N 15/00* (2006.01)
*C07H 21/04* (2006.01)

(52) U.S. Cl.
USPC ..... 435/115; 435/183; 435/252.3; 435/320.1; 536/23.2

(58) Field of Classification Search .................. None
See application file for complete search history.

(56) References Cited

U.S. PATENT DOCUMENTS

| | | |
|---|---|---|
| 6,995,002 B2 | 2/2006 | Molenaar et al. |
| 2004/0002143 A1 | 1/2004 | Asakura et al. |

FOREIGN PATENT DOCUMENTS

| | | | |
|---|---|---|---|
| EP | 1108790 A2 | * | 6/2001 |
| JP | 7-121228 B | | 12/1995 |
| KR | 2001-0051915 A | | 6/2001 |
| KR | 2001-0062279 A | | 7/2001 |
| WO | WO-00/18935 A1 | | 4/2000 |
| WO | WO03040681 A2 | * | 5/2003 |

OTHER PUBLICATIONS

Accession ADD135710, Jan. 1, 2004.*
Eggeling, L. "Biology of L-Lysine Overproduction by *Corynebacterium glutamicum*," Amino Acids (1994), vol. 6, pp. 261-272.
Hilliger, M. "Botechnologische Aminosaureproduktion," BioTec Mikrobiologie (1991), No. 2, pp. 40-42.
Jetten, M.S.M and Sinskey, A. J., "Recent Advances in the Physiology and Genetics of Amino Acid-Producing Bacteria," Critical Reviews in Biotechnology (1995), vol. 15, No. 1, pp. 73-103.
Kinoshita, S., "Glutamic Acid Bacteria," Biology of Industrial Microorganisms. Eds. Arnold L. Demain and Nadine A. Solomon. Menlo Park: The Benjamin/Cummings Publishing Company, Inc., (1985) pp. 115-142.
Sahm, H. et al., "Construction of L-Lysine-, L-Threonine-, or L-Isoleucine- Overproducing Strains of *Corynebacterium glutamicum*," Annals New York Academy of Sciences (1996), vol. 782, pp. 25-39.
Spackman, D. H. et al., "Automatic Recording Apparatus for Use in the Chromatography of Amino Acids," Analytical Chemistry (1958), vol. 30, No. 7, pp. 1190-1206.
van der Rest, M. E. et al., "A heat shock following electroporation induces highly efficient transformation of *Corynebacterium glutamicum* with xenogeneic plasmid DNA," Applied Microbiology and Biotechnology (1995), vol. 52, pp. 541-545.

* cited by examiner

*Primary Examiner* — Christian Fronda
(74) *Attorney, Agent, or Firm* — Birch, Stewart, Kolasch & Birch, LLP

(57) ABSTRACT

The present invention relates to a microorganism of *Corynebacterium* ssp. having enhanced expression of gene for encoding molybdenum cofactor biosynthesis enzyme A and a method for producing L-lysine using the same, which has effects on providing the production method of L-lysine using the *Corynebacterium* strain having enhanced productivity of L-lysine by intensifying expression of the moaA gene for encoding molybdnum cofactor biosynthesis enzyme A.

4 Claims, 1 Drawing Sheet

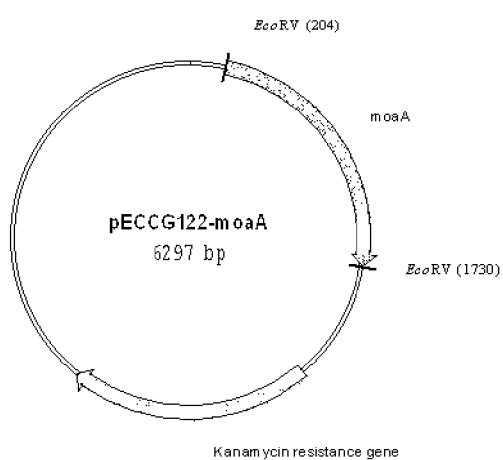

CORYNEBACTERIUM GLUTAMICUM ENHANCED EXPRESSION OF MOAA GENE ENCODING MOLYBDENUM COFACTOR BIOSYNTHESIS ENZYME A AND METHOD FOR PRODUCING L-LYSINE USING THE SAME

TECHNICAL FIELD

The present invention relates to a microorganism of *Corynebacterium* ssp. having enhanced expression of gene for encoding molybdenum cofactor synthesis enzyme A and a method for producing L-lysine using the same. More particularly, the present invention relates to a transformated strain having enhanced activity of molybdenum cofactor biosynthesis enzyme A(moaA) in *Corynebacterium* than its implicit activity and a method for producing L-lysine using the same.

BACKGROUND ART

*Corynebacterium*, especially *Corynebacterium glutamicum* is gram positive microorganism which have been largely used for producing L-amino acid. L-amino acid, especially L-lysine is mainly produced by the fermentation with *Corynebacterium* strain, which is used in an animal feed and human medicine and cosmetics industries.

On this wise, a diversity of attempt have been performed to improve a production method of L-amino acid using *Corynebacterium glutamicum* since it holds an important position in industries.

Particularly, there have been many researches that each of genes relating to L-amino acid biosynthesis is amplified by the DNA recombination technique to examine effects on the formation of L-amino acid and thus to improve *Corynebacterium* strain for producing L-amino acid [Kinoshita, "glutamic acid bacteria" in Biology of industrial Microorganisms, Demain and Solomon (Eds), Benjamin Chummings, London, UK, 1985, 115-142; Hilinger, BioTec 2, 40-44 (1991); Eggeling, *Amino Acids* 6, 261-272 (1994); Jetten and Sinskey, *Critical Reviews in Biotechnology* 15, 73-103 (1995); and Sahm et al., Annuals of the New York Academy of Acience 782, 25-39 (1996)].

In addition, research have been performed by the destruction or the underexpression of a specific gene to improve *Corynebacterium* strain which produces L-amino acid. For example, the Korean Published Patent Application Nos. 2001-51915 and 2001-62279 in the name of Degusa-Huels Acktiengeselshaft disclosed method for enhancing the productivity of L-amino acid from *Corynebacterium* by the under-expression of sucC and sucD gene and zwa2 gene derived from *Corynebacterium glutamicum*.

In addition, it is disclosed a method for introducing gene from other bacteria in the outside. For example, the Japanese Patent No. H07-121228 disclosed method for introducing a gene for encoding citric acid synthase from *Eskerikia Coli*.

On the one hand, molybdenum is an essential transition element functioning as an important role in the biological world, which is required in enzymes catalyzing a diversity of essential reaction in the metabolism of carbon, sulfur and nitrogen. However, since molybdenum itself does not have biological activity, it should be formed a complex with pterin mixture in cell to have proper activity, which is called a molybdenum cofactor. Because a path of a molybdenum cofactor biosynthesis is evolutionally well preserved, many proteins and its gene participating in the path have high homogeny from bacteria to a higher animal comprising human being.

In a biosynthesis process of molybdenum cofactor, guanosine triphosphate converts into molybdopterine precursor Z and then it converts into molybdopterine, and lastly molybdenum combines to them.

The molybdenum cofactor biosynthesis enzyme A which is involved in the first step in the process of molybdenum cofactor biosynthesis, has a role together with molybdenum cofactor biosynthesis enzyme C in converting guanosine triphosphate into molybdopterine precursor Z.

Some of more than 50 species of enzymes which is known by containing molybdenum cofactor in bacteria, participate in the core reaction of nitrogen metabolism procedure. For example, nitrate reductase acts as a major enzyme which is catalyzed a metabolism of inorganic nitrogen source via the reaction of reducing nitrate to nitrite. Moreover, in the production of L-lysine having two nitrogen atoms per a molecular, the nitrogen metabolism can be very important.

Based on the above fact, we kept on trying to increase an activity of enzymes involved in nitrogen metabolism by intensifying the biosynthesis of molybdenum cofactor, through which it can be made smooth supply of nitrogen atom to enhance production efficacy of L-lysine such that the present invention was contrived.

DISCLOSURE OF INVENTION

Technical Problem

The object of the present invention is to intensify molybdenum cofactor biosynthesis to provide *Corynebacterium* strain for producing L-lysine having enhanced L-lysine productivity.

The other object of the present invention is to provide a method for producing L-lysine with the above strain.

Technical Solution

The above object can be achieved by cloning a moaA gene for encoding molybdenum cofactor biosynthesis enzyme A from *Corynebacterium* into coryneform bacteria-*E. coli* shuttle vector pECCG122 and then transforming it into the strain for producing L-lysine to prepare a recombinant bacteria strain having enhanced expression of molybdenum cofactor biosynthesis enzyme A and then culturing the strain to produce L-lysine.

Advantageous Effects

The present invention relates to the microorganism of *Corynebacterium* ssp. having enhanced expression of gene for encoding molybdenum cofactor biosynthesis enzyme A and the method for producing L-lysine using the same, which has effects on providing the production method of L-lysine with the *Corynebacterium* strain having enhanced productivity of L-lysine by intensifying expression of moaA gene for encoding molybdenum cofactor biosynthesis enzyme A.

BRIEF DESCRIPTION OF THE DRAWINGS

FIG. 1 is showing a moaA gene expression vector pECCG122-moaA of the present invention.

BEST MODE FOR CARRYING OUT THE INVENTION

The present invention comprises a step of preparing a transformant strain of *Corynebacterium* having enhanced expression of moaA gene and a step of culturing the strain with a direct culturing method and accumulating L-lysine in fermented liquid and then recovering L-lysine.

The present invention provides a microorganism having productivity of L-lysine, preferably a microorganism of Corynebacterium having enhanced productivity of L-lysine by increasing activity of molybdenum cofactor biosynthesis enzyme A.

In the present invention, an activation of enzyme can be achieved by the well-known method in the art. The term "activation" in the present invention means that gene is produced in higher level than in wild strain by an expression of the gene for encoding molybdenum cofactor biosynthesis enzyme A.

In the present invention, the activation of enzyme is performed by expressing whole of expression unit comprising a promoter part of the gene for encoding molybdenum cofactor biosynthesis enzyme A.

In particular embodiment of the present invention, the activation can be performed by transforming vector comprising the sequence No. 1 into microorganism of Corynebacterium and culturing it and then selecting in order to express whole of expression unit comprising the promoter part of the gene for encoding molybdenum cofactor biosynthesis enzyme A.

In the present invention, it have been used a method for inserting a recombinant expression vector to Corynebacterium to express moaA having enhanced function, however moaA gene can be expressed by using well-known method, such as method for infection of virus to express a foreign gene besides a recombinant expression vector, but not limited to those.

In the present invention, it is characterized in that the microorganism of Corynebacterium ssp. for producing L-lysine is Corynebacterium glutamicum CA01-015 (KCCM-10802P) having enhanced activity of molybdenum cofactor biosynthesis enzyme A than internal activity.

The present invention also provides a method for producing L-lysine by fermentative-culturing the microorganism of Corynebacterium ssp. or its culture solution.

The term "transformation" in the present invention means a method that a gene is introduced into a host cell to be expressed in the host cell. Transformant genes, if they are in the state of being expressed in the host cell, comprise any of genes inserted in chromosome of host cell or positioned in other parts of chromosome. In addition, the gene comprises DNA and RNA as polynucleotide capable of encoding polypeptide. It doesn't matter, if the gene can be introduced in the host cell and expressed therein, that the gene introduces in any type. For example, the gene can be introduced into the host cell in the type of expression cassette which is polynucleotide expressome comprising by it self whole elements for expressing the gene. The expression cassette comprises promoter which is actuatablly connected to the gene, transcription terminating signal, ribosome part and translation terminating signal. The expression cassette can be in the type of the expression vector capable of self cloning. The gene also can be introduced into the host cell by itself or in the type of polynucleotide expressome to actuatablly connected to the sequence necessary for expressing the host cell.

Corynebacterium strain used according to the present invention can be cultured by a continuous or a batch method in batch process or fed batch or repeated fed batch process. Such well-known culturing method disclosed in Chmiel (Bioprozesstechnik 1. Einfuhrung in die Bioverfahrenstechnik (Gustav Fischer Verlag, Stuttgart, 1991)); and Storhas (Bioreaktoren and periphere Einrichtungen (Vieweg Verlag, Braunschweig/Weisbaden, 1994)).

A culturing medium used in the present invention must be fulfilled the requisite of certain strain with an adequate method. The culturing medium for Corynebacterium strain can be found in Manual of Methods for General Bacteriology by the American Society for Bacteriology (Washington D.C., USA, 1981).

Sugar source capable of using in culturing medium for microorganism comprise sugar and carbohydrate such as glucose, saccharose, lactose, fructose, maltose or starchm cellulose, oil and fat such as soybean oil, sunflower oil, castor oil, coconut oil, fatty acid such as palmitic acid, stearic acid or linoleic acid, alcohol such as ethanol, organic acid such as acetic acid. Such material can be used independently or as a mixture.

Nitrogen source for medium include peptone, yeast extract, beef stock, malt extract, corn digestive solution, soybean powder and urea or inorganic compound, for example, ammonium sulfate, ammonium chloride, ammonium phosphate, ammonium carbonate and ammonium nitrate. Nitrogen source also can be used independently or as a mixture.

Phosphorous source for medium include dihydrogen ammonium phosphate or dihydrogen potassium phosphate or corresponding sodium-containing salt.

Culturing medium also must contain metal salt such as magnesium sulfate or iron sulfate.

Lastly, in addition to the above materials, essential growth material such as amino acid and vitamin can be used. Also, precursor suitable for culturing medium can be used. The above materials can be added to medium with batch or continuous process by the adequate method in the course of culturing. The pH of medium can be controlled by the adequate method with the fundamental compound such as odium hydrate, potassium hydrate, ammonia, or acidic compound such as phosphoric acid or sulfuric acid.

In addition, the formation of bubble can be inhibited by using an antiforming agent such as fatty acid polyglycol ester. In order to maintain aerobic state, oxygen or oxygen-containing gas(e.g. air) can be injected.

The temperature of culture product is generally 20 to 45° C., preferably 25 to 40° C. Culture is continued until the desired level of L-amino acid production will be obtained. This is achieved within 10 to 160 hours. L-lysine can be discharged to the culture medium or can be incorporated in the cell.

L-amino acid can be analyzed by anion exchange chromatography and following ninhydrin derivatization [Spackman et al. Analytical Chemistry, 30, (1958), 1190].

MODE FOR THE INVENTION

In the followings, the present invention will be described with reference to examples. However, such examples are only to illustrate the invention and they not restrict the present invention.

EXAMPLE 1

Production of moaA Expression Vector from Corynebacterium

The sequence information of molybdenum cofactor biosynthesis enzyme A in Corynebacterium was obtained from NIH GenBank (moaA; Sequence No.1). In order to increase the activity of moaA gene on genome of Corynebacterium, it was intend to introduce the expression vector for enhancing expression of moaA gene into the cell. In order to amplify whole of the expression unit comprising promoter of moaA gene, a pair of primer(Sequence Nos. 2 and 3) was synthesized based on the reported sequence, and genetic fragment of moaA was amplified in the mould of chromosome DNA of wild type *Corynebacterium glutamicum* (ATCC13032) by the PCR method [Sambrook et al., Molecular Cloning, a Laboratory Manual (1989), Cold Spring Harbor Laboratories] (Conditions: Denaturing=96° C., 30 sec/Annealing=52° C., 30 sec/Polymerization=72° C., 2 min, 30 times). Corineform bacteria-*E. coli* shuttle vector pEGCCG122 which is produced and possessed by the applicant was treated with restriction enzyme EcoRV and then was connected to the product of moaA genetic fragment amplification by using ligation enzyme to produce pECCG122-moaA (see FIG. 1).

EXAMPLE 2

Production of Microorganism for Producing L-Lysine Having Enhanced Expression of moa A Gene pECCG122-moaA produced in Example 1 was transformed to *Corynebacterium glutamicum* KFCC10881 using the electric pulse method [transformation method of Appl. Microbiol. Biotechnol (1999) 52:541-545], and then was coated on LB agar medium containing 25☐/mL of kanamycin followed by selecting and obtaining transformant strain (CA01-015), and then pECCG122-moaA was separated from each transformant strain and confirmed them.

EXAMPLE 3

Production of Lysine from Microorganism for Producing L-Lysine Having Enhanced Expression of moaA Gene In order to produce L-lysine, *Corynebacterium glutamicum* CA01-015 obtained in Example 2 was cultured as follows:

Species medium (pH 7.0): (based on 1 L of processing water)

Raw sugar 20 g, peptone 10 g, yeast extract 5 g, urea 1.5 g, $KH_2PO_4$ 4 g, $K_2HPO_4$ 8 g, $MgSO_4$ $7H_2O$ 0.5 g, biotin 100☐, tiamin HCl 1000☐, potassium-pantotenic acid 2000☐ and nicotineamide 2000☐.

Producing medium (pH 7.0): (based on 1 L of processing water)

Raw sugar 100 g, $(NH_4)2SO_4$ 40 g, soybean protein 2.5 g, Corn Steep Solids 5 g, urea 3 g, $KH_2PO_4$ 1 g, $MgSO_4$ $7H_2O$ 0.5 g, biotin 100☐, tiamin hydrochloride 1000☐, potassium-pantotenic acid 2000☐, nicotineamide 3000☐ and $CaC_3O$ 30 g.

To 250 mL of corner-baffle flask containing 25 mL of species medium, *Corynebacterium glutamicum* KFCC10881 and CA01-015 were seeded and cultured by shaking (200 rpm) at 30° C. for 20 hours. To 250 mL of corner-baffle flask containing 24 mL of producing medium, 1 mL of species culture liquid was seeded and cultured by shaking (200 rpm) at 30° C. for 120 hours.

After culturing, the production amount of L-lysine was determined by the amino acid analyzer and the result was showed in Table 1.

TABLE 1

| Strain | Production of L-lysine(g/L) | | | Increasing rate of L-lysine compared to mother strain | | |
|---|---|---|---|---|---|---|
|  | Bach 1 | Bach 2 | Bach 3 | Bach 1 | Bach 2 | Bach 3 |
| KFCC-10881 | 45 | 45.2 | 44.7 | 4.2% | 4% | 4.1% |
| CA01-015 | 46.9 | 47 | 46.5 | | | |

As shown in Table 1, it was confirmed that the concentration of L-lysine in *Corynebacterium glutamicum* CA01-015 was increase in 4.1% compared with *Corynebacterium glutamicum* KFCC10881.

Hence, *Corynebacterium glutamicum* CA01-015 having enhanced activity of molybdenum cofactor biosynthesis enzyme A than internal activity was deposited the Korean Culture Center of Microorganism attached to the Korean Federation of Culture Collection on Nov. 27, 2006 and a deposition No. KCCM-10802P was obtained.

The invention claimed is:

1. An isolated transformed *Corynebacterium* ssp. strain with enhanced L-lysine productivity comprising:
a nucleic acid comprising SEQ ID NO: 1, wherein SEQ ID NO: 1 encodes molybdenum cofactor biosynthesis enzyme A (moaA) and wherein the moaA is expressed in the transformed strain at a higher level in comparison to an untransformed strain, thereby resulting in enhanced moaA activity and enhanced L-lysine productivity.

2. The isolated transformed *Corynebacterium* ssp. strain of claim 1, wherein the nucleic acid is a vector comprising the whole of an expression unit comprising a promoter part of the gene for encoding moaA.

3. The isolated transformed *Corynebacterium* ssp. strain of claim 1, wherein the *Corynebacterium* ssp. strain is *Corynebacterium glutamicum* CA01-015 deposited under the number KCCM-10802P.

4. A method for producing L-lysine comprising:
fermentative culturing of the isolated transformed *Corynebacterium* ssp. strain of claim 1 in a medium to produce and accumulate L-lysine in the medium, and recovering of the L-lysine from the culture.

* * * * *

SEQUENCE LISTING

```
<160> NUMBER OF SEQ ID NOS: 3

<210> SEQ ID NO 1
<211> LENGTH: 1134
<212> TYPE: DNA
<213> ORGANISM: Corynebacterium glutamicum

<400> SEQUENCE: 1
atgactactc gcctttatct ttcgccaacg ccgccccgaa atgatcggga gggggcgtcg      60
aaaagcactt ctgcgagcat caaacatgat gcgtacctgc cacccgcaga cggcaatcgc     120
gtgcttgtgg acagattcgg acgcatcgcg cgtgacctgc gggtgtcact gaccgaccga     180
tgcaacctcc gctgcaccta ttgcatgccc gcggagggtt tagagtggct gcccaccgag     240
cagacgctta acgacgccga ggtgctgcga ctcatccgca ttgcggtggt taagctgggc     300
attcgtcaaa ttcgattcac cggcggcgag cctttactgc ggaaaaattt ggaagacatc     360
atcgccggca ccgcagccct gcgcaccgac gaaggcgaaa aagttcacat cgctctcacc     420
accaacggcc ttggcctaga caaacgcatc gcaggactga agaagctggg tcttgaccgg     480
gtcaatattt cactcgacac catcgacgcc gaacgctacg tctcgctaac caggcgtgat     540
```

```
cgattgtccg gtgtgttggc gtccatcgat gccgctgttg ccgctggcct tcacccagtg    600
aagatcaacg ccgtggtcat gcctggggtc aatgaagtag atatcgtccc ccttgcggaa    660
tactgcattt ccaaaggctc ccaactgcga ttcatcgaac aaatgccact tggcccgcgc    720
gagcagtgga aacgcggcga tatggtcaca gccgaagaaa tcctggcgcg cctggaagaa    780
aaattcacct tatcccccgc caaggaaccc cgaggagctg cacctgctgc gctgtggaat    840
gtggtagata aatccaaccc tgatatcact ggacaaatcg gcatcatcgc ctcggtgacg    900
cacccatttt gcggagattg cgatcgctcc cgcctcacca ccgacggcac catccgaaac    960
tgccttttct cccgcactga aactcccta cgtgacgcgc ttcgcgacgg cgcctccgac   1020
gatgagctcg cgcaactgtg ggcaggcgcc atgtgggaga agaaacccgg ccatggcatc   1080
gacgatgaag gcttcctcca accagatcgc cccatgtctg ccatcggtgg ctag         1134

<210> SEQ ID NO 2
<211> LENGTH: 19
<212> TYPE: DNA
<213> ORGANISM: Artificial Sequence
<220> FEATURE:
<223> OTHER INFORMATION: Synthetic primer 1 to amplify a whole region of
      moaA gene

<400> SEQUENCE: 2
ctcagctgga aaacctcat                                                  19

<210> SEQ ID NO 3
<211> LENGTH: 20
<212> TYPE: DNA
<213> ORGANISM: Artificial Sequence
<220> FEATURE:
<223> OTHER INFORMATION: Synthetic primer 2 to amplify a whole region of
      moaA gene

<400> SEQUENCE: 3
ttggcgaaaa gtctatgatt                                                 20
```